(12) United States Patent
Sato et al.

(10) Patent No.: US 7,714,155 B2
(45) Date of Patent: May 11, 2010

(54) ALKOXIDE COMPOUND, MATERIAL FOR THIN FILM FORMATION, AND PROCESS FOR THIN FILM FORMATION

(75) Inventors: Hiroki Sato, Tokyo (JP); Atsushi Sakurai, Tokyo (JP)

(73) Assignee: Adeka Corporation, Tokyo (JP)

( * ) Notice: Subject to any disclaimer, the term of this patent is extended or adjusted under 35 U.S.C. 154(b) by 952 days.

(21) Appl. No.: 10/588,187

(22) PCT Filed: Feb. 14, 2005

(86) PCT No.: PCT/JP2005/002118

§ 371 (c)(1),
(2), (4) Date: Aug. 2, 2006

(87) PCT Pub. No.: WO2005/085175

PCT Pub. Date: Sep. 15, 2005

(65) Prior Publication Data

US 2009/0035464 A1    Feb. 5, 2009

(30) Foreign Application Priority Data

Feb. 18, 2004    (JP) .............................. 2004-041427

(51) Int. Cl.
*C07F 7/00* (2006.01)
*C07F 7/10* (2006.01)
*C23C 16/00* (2006.01)

(52) U.S. Cl. .................... 556/56; 556/413; 427/255.28
(58) Field of Classification Search ................... 556/56, 556/413; 427/255.28
See application file for complete search history.

(56) References Cited

U.S. PATENT DOCUMENTS

| 6,274,195 B1 | 8/2001 | Rhee et al. |
| 2003/0059536 A1 | 3/2003 | Rhee et al. |

FOREIGN PATENT DOCUMENTS

| EP | 0 614 867 | 3/1994 |
| JP | 6-321824 | 11/1994 |
| JP | 2000-351784 | 12/2000 |
| JP | 2003-119171 | 4/2003 |
| KR | 2003-74986 | 9/2003 |

OTHER PUBLICATIONS

Lim et al., 10 Surf. Rev. Lett., 685-89 (2003).*
Anwander et al., "Volatile Donor-Functionalized Alkoxy Derivatives of Lutetium and Their Structural Characterization," *Inorganic Chemistry*, vol. 36, No. 16, 1997, pp. 3545-3552.
Wang Yong-zhen et al. 1. Lanzhou University, Lanzhou 730000, China 2. Lanzhou Institute of Physics, Lanzhou 73000, China, Preparation and Application of SiO2 Thin Films, Vacuum & Cryogenics, vol. 9, pp. 228-233, Dec. 2003.
Mehrota, Ram C. et al., Aminoalkoxysilanes I. Amino derivatives of alkoxy-and alkylalkoxysilanes, Journal of Organometallic Chemistry, 1970, 24(3), 611-621.
Abbott, A. Doyle et al., Silicate esters and related compounds, Journal of Chemical and Engineering Data, 1961, 6, 437-442.
Song, Moon-Kyun et al., Direct liquid injection metal-organic chemical vapor deposition of Hf02 thin films using Hf (dimethylaminoethoxide)4, Thin Solid Films, 2004, 450(2), 272-275.

* cited by examiner

*Primary Examiner*—Porfirio Nazario Gonzalez
(74) *Attorney, Agent, or Firm*—Young & Thompson

(57) ABSTRACT

An alkoxide compound of formula (I) suitable as a material for thin film formation used in thin film formation involving vaporization of a material such as CVD, a material for thin film formation including the alkoxide compound, and a process for thin film formation using the material. The process includes vaporizing the material for thin film formation, introducing the resulting vapor containing the alkoxide compound, onto a substrate, and causing the vapor to decompose and/or chemically react to form a thin film on the substrate.

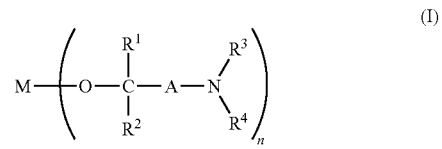

wherein one of $R^1$ and $R^2$ represents an alkyl group having 1-4 carbon atoms, the other representing a hydrogen atom or an alkyl group having 1-4 carbon atoms; $R^3$ and $R^4$ each represent an alkyl group having 1-4 carbon atoms; A represents an alkanediyl group having 1-8 carbon atoms; M represents a silicon atom or a hafnium atom; and n represents 4.

4 Claims, 1 Drawing Sheet

ALKOXIDE COMPOUND, MATERIAL FOR THIN FILM FORMATION, AND PROCESS FOR THIN FILM FORMATION

TECHNICAL FIELD

This invention relates to a novel alkoxide compound having a specific amino alcohol as a ligand (including a silicon alkoxide compound and a hafnium alkoxide compound), a material for thin film formation containing the alkoxide compound, and a process for forming a thin film containing silicon and/or hafnium using the material.

BACKGROUND ART

A thin film containing silicon or hafnium is chiefly used as a member of electronic components, such as high dielectric constant capacitors, ferroelectric capacitors, gate insulators, and barrier films.

Processes for forming the above-described thin film include flame hydrolysis deposition, sputtering, ion plating, MOD techniques including dipping-pyrolysis process and sol-gel process, and chemical vapor deposition (hereinafter sometimes abbreviated as CVD). Chemical vapor deposition processes inclusive of ALD (atomic layer deposition) are the most suitable for many advantages, such as compositional controllability, excellent step coverage, suitability to large volume production, and capability of hybrid integration.

MOD and CVD processes use a compound having an organic ligand as a precursor supplying a metal to a thin film. Reported organic ligands include an alcohol having an ether group or a dialkylamino group at the terminal which provides a relatively high vapor pressure and is suited to thin film formation by CVD. As for silicon, a silicon alkoxide compound having an alkoxy-terminated alcohol as a ligand is described in Patent Document 1. Patent Document 2 and Patent Document 3 disclose a titanium compound and a zirconium compound as a metal compound having, as a ligand, an alcohol terminated with an amino group that is a donor group capable of coordinating to a metal atom. A lanthanide compound is reported in Non Patent Document 1

Patent Document 4 discloses an alkoxide compound having a primary amino alcohol as a ligand.

DISCLOSURE OF THE INVENTION

Patent Document 1: JP-A-6-321824
Patent Document 2: JP-A-2000-351784
Patent Document 3: JP-A-2003-119171
Patent Document 4: Korean unexamined patent publication No. 2003-74986
Non Patent Document 1: *Inorganic Chemistry*, vol. 36, No. 16, 1997, pp. 3545-3552

Compounds (precursors) suitable as a material in thin film formation processes involving vaporization of a compound, such as CVD, are required to have a low melting point and therefore be deliverable in a liquid state and to have a high vapor pressure and therefore be easy to vaporize. Where two or more compounds are used to form a multi-component thin film, the compounds are required not to undergo modification by ligand exchange or any chemical reaction when mixed up or while stored and to exhibit similar behavior in decomposition by heat and/or oxidation associated with thin film deposition. However, there is no compound of silicon or hafnium that sufficiently satisfies these requirements.

As a result of extensive investigations, the present inventors have found that an alkoxide compound having a specific amino alcohol as a ligand provides a solution to the above problem and thus reached the present invention.

The present invention provides an alkoxide compound represented by general formula (I) shown below, a material for thin film formation comprising the alkoxide compound, and a process for thin film formation comprising vaporizing the material for thin film formation according to claim 5, introducing the resulting vapor containing the alkoxide compound, onto a substrate, and causing the vapor to decompose and/or chemically react to form a thin film on the substrate.

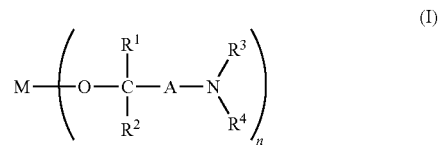

wherein one of $R^1$ and $R^2$ represents an alkyl group having 1 to 4 carbon atoms, and the other represents a hydrogen atom or an alkyl group having 1 to 4 carbon atoms; $R^3$ and $R^4$ each represent an alkyl group having 1 to 4 carbon atoms; A represents an alkanediyl group having 1 to 8 carbon atoms; M represents a silicon atom or a hafnium atom; and n represents 4.

BEST MODE FOR CARRYING OUT THE INVENTION

Figure 1:
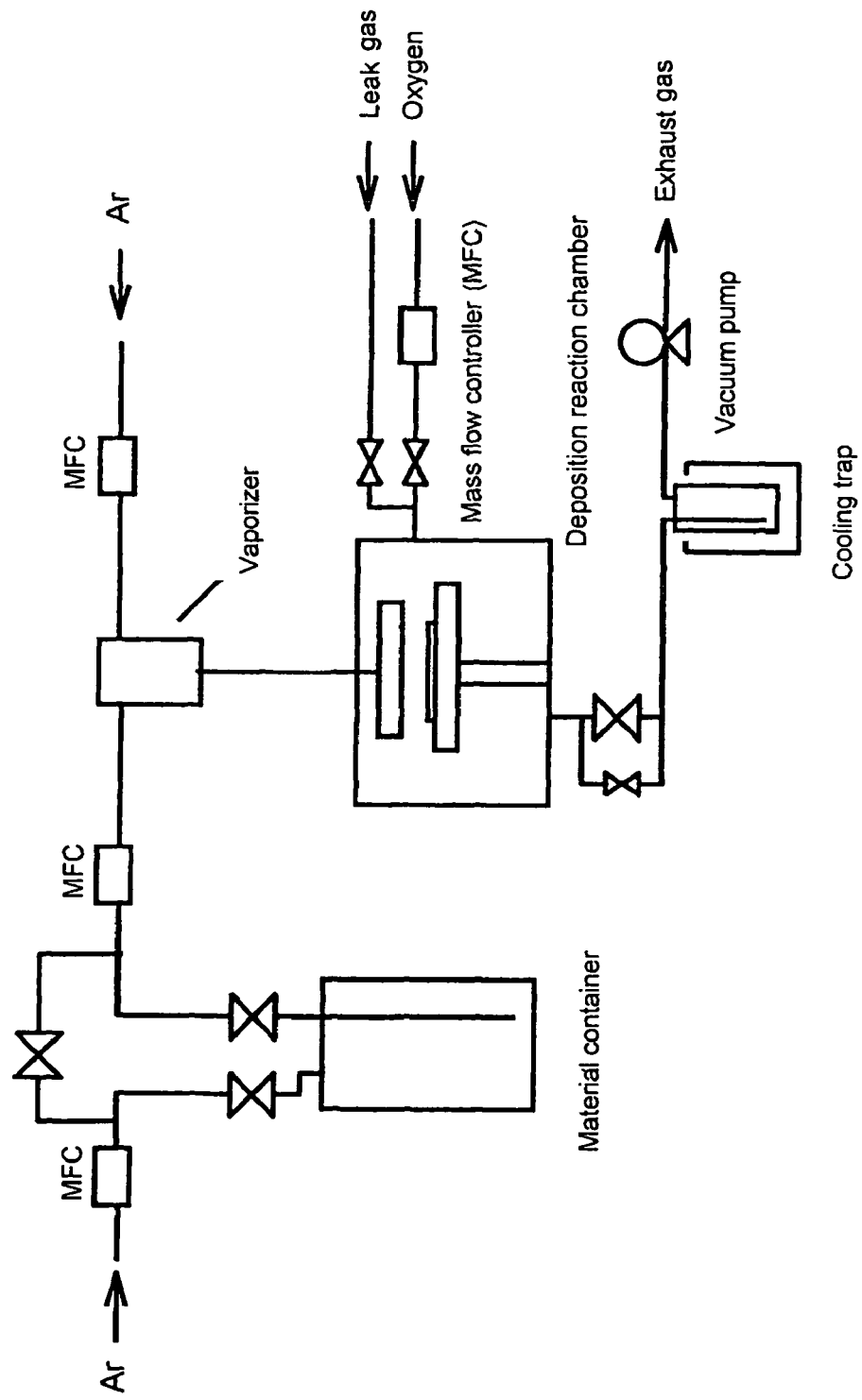
FIG. 1 is a schematic diagram illustrating an example of a CVD system that can be used to carry out the thin film formation process according to the invention.

The alkoxide compound of the present invention is represented by general formula (I) and is particularly suitable as a precursor in thin film formation processes involving vaporization, such as CVD and ALD.

Compared with well-known silicon alkoxide compounds, a silicon alkoxide compound of general formula (I) in which M is a silicon atom has high decomposability by heat and/or oxygen and high stability to chemical reaction. Furthermore, it has a higher vapor pressure than a structurally similar alkoxide compound having a primary amino alcohol as a ligand. Therefore, the silicon alkoxide compound of the present invention is energetically profitable in thin film formation when used alone. When used in combination with other precursor(s), the silicon alkoxide compound is advantageous in thin film composition control because it is ready to keep in line with the other precursors in decomposing behavior. Moreover, it can be used as mixed with the other precursor, which offers operational advantages.

Compared with well-known hafnium alkoxide compounds, a hafnium alkoxide compound of general formula (I) in which M is a hafnium atom has comparable or superior decomposability by heat and/or oxygen and high stability to chemical reaction. Furthermore, it has a higher vapor pressure than a structurally similar alkoxide compound having a primary amino alcohol as a ligand. Therefore, the hafnium alkoxide compound of the invention is energetically profitable in thin film formation when used alone. When used in combination with other precursor(s), it is advantageous in thin film composition control because it is ready to keep in line with the other precursors in decomposing behavior.

Moreover, it can be used as mixed with the other precursor, which offers operational advantages.

In general formula (I), the alkyl group having 1 to 4 carbon atoms as represented by $R^1$, $R^2$, $R^3$, and $R^4$ includes methyl, ethyl, propyl, isopropyl, butyl, sec-butyl, tert-butyl, and isobutyl. The alkanediyl group as represented by A may have a straight-chain configuration or may have one or more branches at any position(s) as long as the total carbon atom number is from 1 to 8. The alkanediyl group is preferably the one which makes an energetically stable 5- or 6-membered ring when the terminal donor group, the dialkylamino group, is coordinated to a silicon atom or a hafnium atom. Such a preferred alkanediyl group includes a group represented by general formula (II) shown below. The alkoxide compound of the present invention can include optical isomers but is not distinguished by the isomeric configuration.

$$\begin{array}{c} R^5 \\ | \\ -C- \\ | \\ R^6 \end{array} \left( \begin{array}{c} R^7 \\ | \\ C \\ | \\ R^8 \end{array} \right)_x \quad (II)$$

wherein $R^5$, $R^6$, $R^7$, and $R^8$ each represent a hydrogen atom or an alkyl group having 1 to 4 carbon atoms; and x represents 0 or 1; provided that the total number of carbon atoms in the formula is 1 to 8.

The compound in which the terminal donor group of the ligand is coordinated to the silicon or hafnium atom to form a cyclic structure is represented by general formula (III) below. The alkoxide compound of the present invention represented by general formula (I) is not distinguished from the compound represented by general formula (III). That is, the alkoxide compound of general formula (I) includes in its scope the compound of general formula (III).

$$\left( M \underset{N}{\overset{O}{\diagdown}} \begin{array}{c} R^1 \\ R^2 \\ A \end{array} \right)_n \quad (III)$$
$$\quad R^3 \quad R^4$$

wherein one of $R^1$ and $R^2$ represents an alkyl group having 1 to 4 carbon atoms, and the other represents a hydrogen atom or an alkyl group having 1 to 4 carbon atoms; $R^3$ and $R^4$ each represents an alkyl group having 1 to 4 carbon atoms; A represents an alkanediyl group having 1 to 8 carbon atoms; M represents a silicon atom or a hafnium atom; and n represents 4.

Specific examples of the alkoxide compound of the present invention include compound Nos. 1 through 22 listed below.

Compound No. 1

$$Si \left( O-CH(-)-CH_2-N \diagup \diagdown \right)_4$$

Compound No. 2 through Compound No. 15 (structural formulas shown).

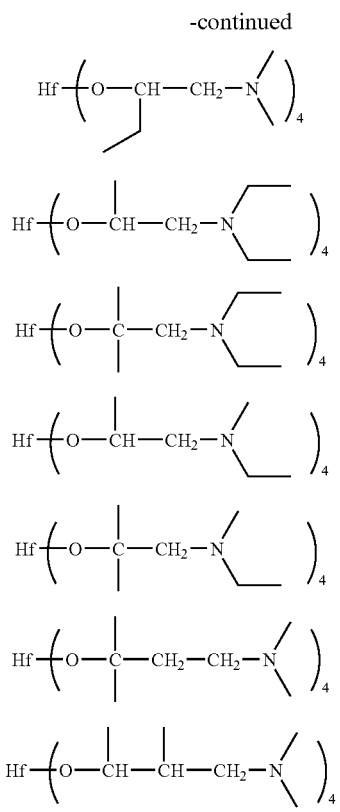

Compound No. 16
Compound No. 17
Compound No. 18
Compound No. 19
Compound No. 20
Compound No. 21
Compound No. 22

Where the alkoxide compound of the present invention is used in thin film formation involving the step of vaporization, it is preferred that $R^1$ to $R^4$ and A in general formula (I) have a smaller molecular weight to provide a higher vapor pressure. Specifically, $R^1$ and $R^2$ are each preferably a hydrogen atom or a methyl group, $R^3$ and $R^4$ are each preferably a methyl group, and A is preferably a methylene group. Where the alkoxide compound of the present invention is used in thin film formation by MOD involving no vaporization step, $R^1$ to $R^4$ and A are selected appropriately according to solubility in the solvent used and reactivity in thin film formation.

The alkoxide compound of the present invention is not limited by the process of preparation and can be prepared by using well-known reactions. Widely known processes for synthesizing general alkoxide compounds can be applied using a corresponding amino alcohol. Such processes include a process comprising reacting a halide or an inorganic salt (e.g., a nitrate) or its hydrate of silicon or hafnium with a corresponding alcohol compound in the presence of a base such as sodium, sodium hydride, sodium amide, sodium hydroxide, sodium methylate, ammonia or amine; a process comprising reacting a halide or an inorganic salt (e.g., a nitrate) or its hydrate of silicon or hafnium with an alkali metal alkoxide (e.g., sodium alkoxide, lithium alkoxide or potassium alkoxide) of a corresponding alcohol compound; a process comprising an alcohol exchange reaction between a silicon or hafnium alkoxide of a low-molecular alcohol, such as a methoxide, ethoxide, isopropoxide or butoxide, and a corresponding alcohol compound; and a process comprising reacting a silicon or hafnium halide or inorganic salt (e.g., nitrate) with a derivative providing a reactive intermediate and reacting the intermediate with a corresponding alcohol compound.

The reactive intermediate includes amide compounds of silicon or hafnium, such as a tetrakis(dialkylamino)silicon, tetrakis(bis(trimethylsilyl)amino)silicon, a tetrakis(dialkylamino)hafnium, and tetrakis(bis(trimethylsilyl)amino) hafnium.

The material for thin film formation according to the present invention contains the aforementioned alkoxide compound of the present invention as a thin film precursor. The form of the material depends on the thin film formation technique using the material, including MOD processes, such as dipping-pyrolysis and sol-gel process, and CVD processes inclusive of ALD. The alkoxide compound of the present invention is especially useful as a raw material of CVD in view of its physical properties.

Where the material for thin film formation of the present invention is for chemical vapor deposition (CVD), the form of the material is selected as appropriate to the procedures of the CVD process adopted, such as a source delivery system.

The source delivery system includes a vapor delivery system in which the material for CVD is vaporized by heating and/or pressure reduction in a container and introduced into a deposition reaction site, if desired, together with a carrier gas, e.g., argon, nitrogen or helium, and a liquid delivery system in which the material for CVD is delivered in the form of a liquid or a solution to a vaporizer, where it is vaporized by heating and/or pressure reduction and then led to a deposition reaction site. When applied to the vapor delivery system, the alkoxide compound represented by general formula (I) per se is a material for CVD. In the case of the liquid delivery system, the alkoxide compound represented by general formula (I) per se or a solution of the compound in an organic solvent is a material for CVD.

In a multi-component CVD process, the source delivery systems includes a system in which a plurality of the materials are separately vaporized and delivered (hereinafter referred to as a multi-source system) and a system in which a plurality of the materials are previously mixed at a prescribed ratio, and the mixture is vaporized and delivered (hereinafter referred to as a single source system). In the case of the single source system, the material for CVD is a mixture or mixed solution of the alkoxide compounds of the present invention or a mixture or mixed solution of the alkoxide compound(s) of the present invention and other precursor(s).

The organic solvent that can be used in the material for CVD is not particularly limited, and any widely known organic solvent is useful. Examples are alcohols, such as methanol, ethanol, 2-propanol, and n-butanol; acetic esters, such as ethyl acetate, butyl acetate, and methoxyethyl acetate; ether alcohols, such as ethylene glycol monomethyl ether, ethylene glycol monoethyl ether, ethylene glycol monobutyl ether, and diethylene glycol monomethyl ether; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine, and lutidine. A solvent or a mixture of solvents to be used is selected according to, for example, solubility for the solute and the boiling temperature or ignition temperature in relation to the working temperature. In using these organic solvents, the total concentration of the alkoxide compounds of the present invention and other precursors in the organic solvent is preferably 0.01 to 2.0 mol/l, still preferably 0.05 to 1.0 mol/l.

Other precursors that can be used in combination with the alkoxide compound of the present invention in the multi-component CVD system are not particularly limited, and any precursors well-known in the art for use as CVD materials can be used.

The other precursors include compounds formed between silicon or a metal and one or more organic coordinating compounds selected from alcohol compounds, glycol compounds, β-diketone compounds, cyclopentadiene compounds, organic amine compounds, and so forth. The metal species of the precursors include magnesium, calcium, strontium, barium, titanium, zirconium, hafnium, vanadium, niobium, tantalum, manganese, iron, ruthenium, cobalt, rhodium, iridium, nickel, palladium, platinum, copper, silver, gold, zinc, gallium, indium, germanium, tin, lead, antimony, bismuth, yttrium, lanthanum, cerium, praseodymium, neodymium, promethium, samarium, europium, gadolinium, terbium, dysprosium, holmium, erbium, thulium, and ytterbium.

The alcohol compounds that can be used as an organic ligand include alkyl alcohols, such as methanol, ethanol, propanol, isopropanol, butanol, 2-butanol, isobutanol, tert-butanol, amyl alcohol, isoamyl alcohol, and tert-amyl alcohol; ether alcohols, such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol; and dialkylamino alcohols providing the alkoxide compounds of the present invention.

The glycol compounds that can be used as an organic ligand include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

The β-diketone compounds that can be used as an organic ligand include alkyl-substituted β-ketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluoroalkyl-substituted β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

The cyclopentadiene compounds that can be used as an organic ligand include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene. The organic amine compounds that can be used as an organic ligand include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

The other precursor, when used in a multi-source system, is preferably a compound that exhibits similar behavior in decomposition by heat and/or oxidation. The other precursor, when used in a single-source system, is preferably a compound that undergoes no modification due to chemical reaction on mixing as well as exhibits similar behavior in decomposition by heat and/or oxidation.

Examples of precursors for titanium or zirconium include tetraalkoxytitaniums having the same ligand as that possessed by the alkoxide compound of the present invention and compounds represented by general formula shown below.

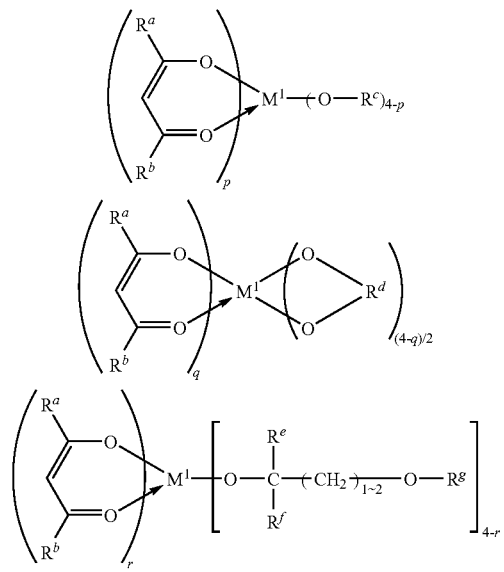

wherein $M^1$ represents titanium or zirconium; $R^a$ and $R^b$ each independently represent an alkyl group having 1 to 20 carbon atoms which may be substituted with a halogen atom and may contain an oxygen atom in its chain; $R^C$ represents an alkyl group having 1 to 8 carbon atoms; $R^d$ represents a straight-chain or branched alkylene group having 2 to 18 carbon atoms; $R^e$ and $R^f$ each represent a hydrogen atom or an alkyl group having 1 to 3 carbon atoms; $R^g$ represents an alkyl group having 1 to 4 carbon atoms; p represents an integer of 0 to 4; q represents 0 or 2; and r represents an integer of 0 to 3.

In the above general formula, the alkyl group having 1 to 20 carbon atoms which may be substituted with a halogen atom and may contain an oxygen atom in its chain as represented by $R^a$ and $R^b$ includes methyl, ethyl, propyl, isopropyl, butyl, sec-butyl, tert-butyl, isobutyl, amyl, isoamyl, sec-amyl, tert-amyl, hexyl, cyclohexyl, 1-methylcyclohexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, and 2-(2-methoxyethoxy)-1,1-dimethylethyl. The alkyl group having 1 to 8 carbon atoms as represented by $R^c$ includes methyl, ethyl, propyl, isopropyl, butyl, sec-butyl, tert-butyl, isobutyl, amyl, isoamyl, sec-amyl, tert-amyl, hexyl, 1-ethylpentyl, cyclohexyl, 1-methylcyclohexyl, heptyl, isoheptyl, tert-heptyl, n-octyl, isooctyl, tert-octyl, and 2-ethylhexyl. The straight-chain or branched alkylene group having 2 to 18 carbon atoms as represented by $R^d$ is a group derived from glycols including 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. The alkyl group having 1 to 3 carbon atoms as represented by $R^e$ and $R^f$ includes methyl, ethyl, propyl, and 2-propyl. The alkyl group having 1 to 4 carbon atoms as represented by $R^g$ includes methyl, ethyl, propyl, isopropyl, butyl, sec-butyl, tert-butyl, and isobutyl.

Specific examples of the titanium precursors include tetrakis(alkoxy)titaniums, such as tetrakis(ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-amyl)titanium, and tetrakis(1-methoxy-2-methyl-2-propoxy)titanium; tetrakis(β-diketonato)titaniums, such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato)titaniums, such as bis(methoxy)bis(pentane-2,4-dionato)titanium, bis(ethoxy)bis(pentane-2,4-dionato)titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato)titanium, bis(tert-butoxy)bis(2,2,6,6-tetramethylheptane-3,5-dionato)titanium, and bis(tert-amyloxy)bis(2,2,6,6-tetramethylheptane-3,5-dionato)titanium; and glycoxybis(β-diketonato)titaniums, such as (2-methylpentanedioxy)bis(2,2,6,6-tetramethylheptane-3,5-dionato)titanium and (2-methylpentanedioxy)bis(2,6-dimethylheptane-3,5-dionato)titanium. Examples of the zirconium precursor include the above-listed titanium precursors with titanium displaced with zirconium.

Examples of aluminum precursors include trialkoxyaluminums having the same ligand as possessed by the alkoxide compound of the present invention and compounds represented by general formula:

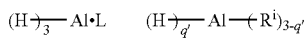

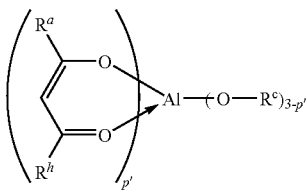

-continued

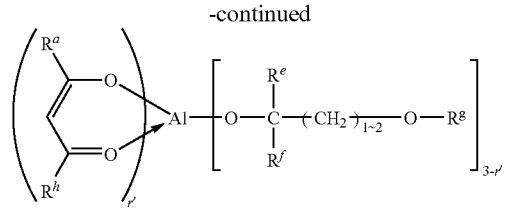

wherein L represents a coordinating 5- or 6-membered heterocyclic compound having a nitrogen atom or an oxygen atom; $R^a$ represents an alkyl group having 1 to 20 carbon atoms which may be substituted with a halogen atom and may contain an oxygen atom in its chain; $R^c$ represents an alkyl group having 1 to 8 carbon atoms; $R^e$ and $R^f$ each represent a hydrogen atom or an alkyl group having 1 to 3 carbon atoms; $R^g$ represents an alkyl group having 1 to 4 carbon atoms; $R^h$ represents an alkyl group having 1 to 20 carbon atoms which may be substituted with a halogen atom and may contain an oxygen atom in its chain or an alkoxy group having 1 to 8 carbon atoms; $R^i$ represents an alkyl group having 1 to 4 carbon atoms; p' represents an integer of 0 to 3; q' represents an integer of 0 to 2; and r' represents an integer of 0 to 2.

In the chemical formula above, the coordinating heterocyclic compound as represented by L includes crown ethers, such as 18-crown-6, dicyclohexyl-18-crown-6, 24-crown-8, dicyclohexyl-24-crown-8, and dibenzo-24-crown-8; cyclic polyamines, such as cyclam and cyclen; pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane. The groups represented by $R^a$, $R^c$, $R^e$, $R^f$, and $R^g$ include the corresponding examples enumerated above with respect to the titanium or zirconium precursors. The alkoxy group having 1 to 8 carbon atoms as represented by $R^h$ includes methyloxy, ethyloxy, propyloxy, isopropyloxy, butyloxy, sec-butyloxy, tert-butyloxy, isobutyloxy, amyloxy, isoamyloxy, sec-amyloxy, tert-amyloxy, hexyloxy, 1-ethylpentyloxy, cyclohexyloxy, 1-methylcyclohexyloxy, heptyloxy, isoheptyloxy, tert-heptyloxy, n-octyloxy, isooctyloxy, tert-octyloxy, and 2-ethylhexyloxy. The group as represented by $R^i$ includes the examples enumerated above as $R^g$.

Bismuth precursors include triarylbismuth compounds, such as trisphenylbismuth, tri(o-methylphenyl)bismuth, tri(m-methylphenyl)bismuth, and tri(p-methylphenyl)bismuth; trialkylbismuth compounds, such as trimethylbismuth; β-diketone complexes, such as tris(2,2,6,6-tetramethylheptane-3,5-dionato)bismuth; cyclopentadienyl complexes, such as tris(cyclopentadienyl)bismuth and tris(methylcyclopentadienyl)bismuth; alkoxides with low molecular alcohols, such as tris(tert-butoxy)bismuth, tris(tert-amyloxy)bismuth, and tris(ethoxy)bismuth; alkoxide compounds represented by general formula shown below; and trisalkoxybismuth compounds having the same ligand as possessed by the alkoxide compound of the invention.

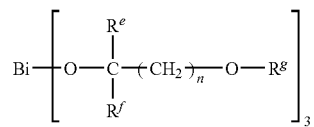

wherein $R^e$ and $R^f$ each represent a hydrogen atom or an alkyl group having 1 to 3 carbon atoms; $R^g$ represents an alkyl group having 1 to 4 carbon atoms; and n represents 1 or 2.

In the general formula above, $R^e$, $R^f$, and $R^g$ include the corresponding groups recited with reference to the titanium precursors and zirconium precursors.

Rare earth precursors include trialkoxide compounds having the same ligand as possessed by the alkoxide compounds of the present invention and compounds represented by general formula:

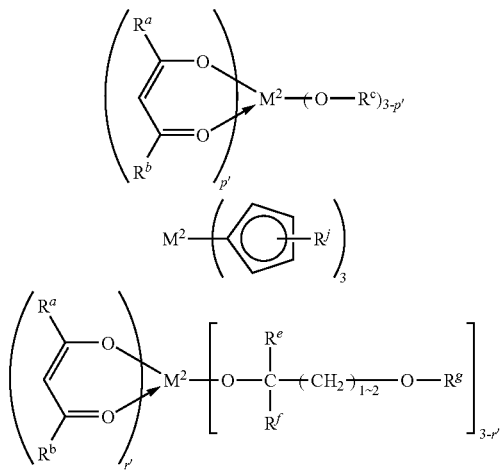

wherein $M^2$ represents a rare earth atom; $R^a$ and $R^b$, each represent an alkyl group having 1 to 20 carbon atoms which may be substituted with a halogen atom and may contain an oxygen atom in its chain; $R^c$ represents an alkyl group having 1 to 8 carbon atoms; $R^e$ and $R^f$ each represent a hydrogen atom or an alkyl group having 1 to 3 carbon atoms; $R^g$ represents an alkyl group having 1 to 4 carbon atoms; $R^j$ represents an alkyl group having 1 to 4 carbon atoms; p' represents an integer of 0 to 3; and r' represents an integer of 0 to 2.

In the rare earth supplying compounds represented by the general formula above, the rare earth atom represented by $M^2$ includes scandium, yttrium, lanthanum, cerium, praseodymium, neodymium, promethium, samarium, europium, gadolinium, terbium, dysprosium, holmium, erbium, thulium, ytterbium, and lutetium. The groups represented by $R^a$, $R^b$, $R^c$, $R^e$, $R^f$, and $R^g$ include the corresponding groups enumerated with reference to the titanium precursors and zirconium precursors. Examples of the alkyl group having 1 to 4 carbon atoms as represented by $R^j$ include those enumerated as for $R^g$.

If desired, the material for CVD can contain a nucleophilic reagent to stabilize the alkoxide compound of the present invention and other precursor. Examples of the nucleophilic reagent include ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines, such as cyclam and cyclen; heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexanedione, 2,4-heptanedione, 3,5-heptanedione, and dipivaroylmethane. The nucleophilic reagent as a stabilizer is used usually in an amount of 0.1 to 10 mol, preferably 1 to 4 mol, per mole of the precursor.

The process for thin film formation according to the present invention is by CVD using the alkoxide compound of the invention and, if necessary, other precursor. CVD is a process in which a vaporized material and, if necessary, a reactive gas is/are led to a substrate and allowed to decompose and/or chemically react on the substrate, and a thin film is allowed to grow and build up on the substrate. The process of the present invention is not particularly restricted by the method of material delivery, the mode of deposition, the film formation conditions, the film formation equipment, and the like. Any conditions and methods commonly known in the art are made use of.

The reactive gas which can be used if necessary includes oxidizing gases, such as oxygen, ozone, nitrogen dioxide, nitrogen monoxide, water vapor, hydrogen peroxide, formic acid, acetic acid, and acetic anhydride; and reducing gases, such as hydrogen. Reactive gases that can be used to form a nitride film include organic amine compounds, such as monoalkylamines, dialkylamines, trialkylamines, and alkylenediamines; hydrazine; and ammonia.

The method of material delivery includes the above-described vapor delivery system, liquid delivery system, single source system, and multi-source system.

The deposition modes include thermal CVD (only heat is used to cause the vaporized material or a mixture of the vaporized material and a reactive gas to react to deposit a film), plasma-enhanced CVD (heat and plasma are used), photo-assisted CVD (heat and light are used), photo plasma-assisted CVD (heat, light, and plasma are used), and ALD (atomic layer deposition) in which a deposition reaction of CVD is divided into elementary reaction steps so as to build up a film stepwise on a molecular level.

The film formation conditions include reaction temperature (the substrate temperature), reaction pressure, and deposition rate. The reaction temperature is preferably 160° C. or higher at which the alkoxide compound of the present invention reacts sufficiently, still preferably 250° to 800° C. The reaction pressure is from atmospheric pressure to 10 Pa for thermal CVD and photo-assisted CVD or from 10 to 2000 Pa for film formation using plasma. The deposition rate can be controlled by the material feed conditions (vaporizing temperature and vaporizing pressure) and the reaction temperature and pressure. A too high deposition rate tends to result in deteriorated characteristics of the resulting thin film, and a too low deposition rate can result in poor productivity. A preferred deposition rate ranges from 0.5 to 5000 nm/min, still preferably 1 to 1000 nm/min. In the case of ALD, the film thickness is controlled by the number of cycles to reach a desired film thickness.

In the process for thin film formation of the present invention, the resulting thin film may be subjected to annealing in an inert, oxidizing or reducing atmosphere to obtain improved electrical characteristics. Where step coverage is required, the process can have the step of reflowing the thin film. The reflow is conducted usually at 400° to 1200° C., preferably 500° to 800° C.

Combined with appropriate selections of a precursor of other component, a reactive gas, and film forming conditions, the material for thin film formation according to the present invention and the process for thin film formation according to the invention provide a thin film of desired kind, such as oxide ceramics, nitride ceramics, and glass. Compositions of the thin films produced in the present invention include silicon oxide, hafnium oxide, silicon-titanium double oxide, silicon-zirconium double oxide, silicon-hafnium double oxide, silicon-bismuth double oxide, hafnium-aluminum double oxide, hafnium-rare earth element double oxide, silicon-bismuth-titanium complex oxide, silicon-hafnium-aluminum complex oxide, silicon-hafnium-rare earth element complex oxide, silicon nitride, and hafnium nitride. Applications of these thin films include elements of electronic parts, such as high dielectric constant capacitor films, gate insulators, gate films ferroelectric capacitor films, capacitor films, and barrier films, and optical glass elements, such as optical fibers, optical waveguides, optical amplifiers, and optical switches.

EXAMPLES

The present invention will now be illustrated in greater detail with reference to Preparation Examples, Evaluation Examples, and Examples, But it should be Understood that the invention is not construed as being limited thereto.

Preparation Examples 1 to 3 represent examples of the alkoxide compound of the present invention; Evaluation Examples 1 and 2 show evaluation of thermo-oxidative decomposability of the alkoxide compounds of the present invention and comparative compounds; Evaluation Examples 3 and 4 show evaluation of vaporization characteristics of the alkoxide compounds of the present invention and comparative compounds; Examples 1 through 3 provide examples of the material for thin film formation of the present invention and the process for thin film formation of the present invention; and Comparative Example 1 presents an example of a material for thin film formation using a compound other than the alkoxide compound of the present invention and thin film formation using the material.

Preparation Example 1

Preparation of Compound No. 1

In a reaction flask were put 0.687 mol of 1-dimethylamino-2-propanol, 500 ml of dehydrated toluene, and 0.481 mol of sodium in a dry argon atmosphere, and the mixture was stirred until solid sodium disappeared. After the inner temperature was adjusted to 4° C., a mixed liquid of 50 ml of dry toluene and 0.1145 mol of silicon tetrachloride was added dropwise to the mixture. The inner temperature was controlled not to exceed 30° C. during the addition. After completion of the addition, the system was refluxed at 120° C. for 27 hours. The reaction mixture was filtered through a 0.2 μm filter, and the filtrate was concentrated by removing the solvent and any unreacted alcohol by evaporation under reduced pressure. The concentrate was distilled under reduced pressure. From the fraction at 25 to 30 Pa and a tower top temperature of 108° to 109° C. was obtain a colorless liquid in a yield of 46%, which was further purified by distillation under reduced pressure to give a clear, colorless liquid. The recovery of the purification was 95%. The resulting clear, colorless liquid was identified to be the title compound, compound No. 1. The analytical values of the clear, colorless liquid were as follows.

Results of Analyses (1) Elemental analysis (metal analysis: ICP-AES)
Si: 6.49% by mass (calcd.: 6.43%); Na: less than 1 ppm; Cl; less than 5 ppm (2) $^1$H-NMR (solvent: deuterobenzene) (chemical shift:multiplicity:number of hydrogens)
(1.46:d:12), (2.18:s:24), (2.27:m:4), (2.53:m:4), (4.44:m:4)

(3) TG-DTA (Ar: 100 ml/min; temperature rise: 10° C./min; amount of sample: 7.762 mg)
50% mass loss temperature: 217° C.

Preparation Example 2

Preparation of Compound No. 2

Into a reaction flask were put 0.687 mol of 1-dimethylamino-2-methyl-2-propanol, 500 ml of dehydrated toluene, and 0.481 mol of sodium in a dry argon atmosphere, and the mixture was stirred until solid sodium disappeared. After the inner temperature was adjusted to 4° C., a mixed liquid of 50 ml of dry toluene and 0.1145 mol of silicon tetrachloride was added dropwise to the mixture. The inner temperature was controlled not to exceed 30° C. during the addition. After completion of the addition, the system was refluxed at 120° C. for 27 hours. The reaction mixture was filtered through a 0.2 μm filter, and the filtrate was concentrated by removing the solvent and any unreacted alcohol by evaporation under reduced pressure. The concentrate was distilled under reduced pressure. From the fraction at 25 to 30 Pa and a tower top temperature of 115° to 118° C. was obtain a colorless liquid in a yield of 52%, which was further purified by distillation under reduced pressure to give a clear, colorless liquid. The recovery of the purification was 95%. The resulting clear, colorless liquid was identified to be the title compound, compound No. 2. The analytical values of the clear, colorless liquid were as follows.

Results of Analyses (1) Elemental analysis (metal analysis: ICP-AES)
Si: 6.10% by mass (calcd.: 6.04%); Na: less than 1 ppm; Cl; less than 5 ppm (2) $^1$H-NMR (solvent: deuterobenzene) (chemical shift:multiplicity:number of hydrogens)
(1.56:s:24), (2.32:s:24), (2.44:s:8)

(3) TG-DTA (Ar: 100 ml/min; temperature rise: 10° C./min; amount of sample: 9.199 mg)
50% mass loss temperature: 233° C.

Preparation Example 3

Preparation of Compound No. 13

In a reaction flask were put dropwise 0.100 mol of tetrakis (2-propoxy)hafnium 2-propanol, 60 ml of dehydrated xylene, and 0.600 mol of 1-dimethylamino-2-methyl-2-propanol in a dry argon atmosphere. The reaction system was allowed to react at 140° C. for 8 hours while distilling off by-produced 2-propanol. Xylene was removed by evaporation, and the residue was distilled under reduced pressure. From the fraction at 25 to 28 Pa and a tower top temperature of 154° to 150° C. was obtain a colorless liquid in a yield of 32%, which was further purified by distillation under reduced pressure to give a clear, colorless liquid. The recovery of the purification was 93%. The resulting clear, colorless liquid was identified to be the title compound, compound No. 13. The analytical values of the clear, colorless liquid were as follows.

Results of Analyses (1) Elemental analysis (metal analysis: ICP-AES)
Hf: 28.2% by mass (calcd.: 27.7%)

(2) $^1$H-NMR (solvent: deuterobenzene) (chemical shift:multiplicity:number of hydrogens)
(1.45:s:24), (2.36:s:24), (2.53:s:8)

(3) TG-DTA (Ar: 100 ml/min; temperature rise: 10° C./min; amount of sample: 7.695 mg)
50% mass loss temperature: 250° C.

Evaluation Example 1

Evaluation of Thermo-Oxidative Decomposability of Silicon Compounds

Compound No. 1 obtained in Preparation Example 1, tetraethoxysilane (TEOS), and comparative compound 1 shown below were evaluated for thermo-oxidative decomposability. Compound No. 1 and comparative compound 1 were analyzed by differential thermal analysis (TG-DTA) under conditions of a temperature rise from 30° C. at a rate of 10° C./min and a dry oxygen stream (100 ml/min). In DTA, the exothermic peak top temperature and the residue at 450° C. were measured for evaluation. The results obtained are shown in Table 1 below.

Because TEOS was unmeasurable by the above method, it was mixed with oxygen in a closed container and heated at 500° C. for 1 minute to examine oxidative decomposition. As a result, oxidative decomposition was not confirmed.

TABLE 1

Comparative Compound 1

$$Si\!-\!(\!O\!-\!\underset{|}{\overset{|}{C}}\!-\!CH_2\!-\!O\!-\!)_4$$

| Compound | Exothermic Peak Top (° C.) | Residue at 450° C. (mass %) | Theoretical Value as SiO$_2$ (mass %) |
|---|---|---|---|
| Compound No. 1 | 205 | 12.8 | 13.8 |
| Comparative Compound 1 | 217 | 5.0 | 13.5 |
| TEOS | — | 0 | 26.3 |

Comparison between compound No. 1 and comparative compound 1 in Table 1 reveals the following: (1) The former has a lower exothermic peak top temperature than the latter. (2) The former has a 450° C. residue close to the theoretical value as SiO$_2$ whereas the 450° C. residue of the latter is far lower than the theoretical value. It is seen from these results that compound No. 1 thermo-oxidatively decomposes at lower temperatures than TEOS and comparative compound 1 and is thus proved superior as a precursor supplying silicon oxide to a thin film being deposited.

Evaluation Example 2

Evaluation of Thermo-Oxidative Decomposability of Hafnium Compounds

Compound No. 13 obtained in Preparation Example 3 and comparative compound 2 shown below were evaluated for thermo-oxidative decomposability in the same manner as in Evaluation Example 1. The results are shown Table 2 below.

TABLE 2

Comparative Compound 2

$$Hf\!-\!(\!O\!-\!\underset{|}{\overset{|}{C}}\!-\!CH_2\!-\!O\!-\!)_4$$

| Compound | Exothermic Peak Top (° C.) | 450° C. Residue (mass %) | Theoretical Value as HfO$_2$ (mass %) |
|---|---|---|---|
| Compound No. 13 | 256 | 30.1 | 32.7 |
| Comparative Compound 2 | 271 | 18.2 | 30.2 |

Comparison between compound No. 13 and comparative compound 2 in Table 2 reveals the following: (1) The former has a lower exothermic peak top temperature than the latter. (2) The former has a 450° C. residue close to the theoretical value as HfO$_2$ whereas the 450° C. residue of the latter is lower than the theoretical value. It is seen from these results that compound No. 13 thermo-oxidatively decomposes at lower temperatures than comparative compound 2 and is thus proved superior as a precursor supplying hafnium oxide to a thin film being deposited.

Evaluation Example 3

Evaluation of Vaporization Characteristics of Silicon Compounds

Vaporization characteristics of compound Nos. 1 and 2 and comparative compound 3 shown below were evaluated by measuring their vapor pressure. Vapor pressure measurement was made by measuring the vapor temperature near the liquid surface under a fixed pressure. The vapor temperature was measured at 3 or 4 points at a varied pressure of the system, and a vapor pressure equation obtained from the Clausius-Clapeyron plot was applied to calculate the vapor pressures at 120° C. and 150° C. The results are shown in Table 3.

TABLE 3

Comparative Compound 3

$$Si\!-\!(\!O\!-\!CH_2\!-\!CH_2\!-\!N\!\!<\!)_4$$

| Compound | Vapor Pressure Equation | Vapor Pressure at 120° C. (Torr) | Vapor Pressure at 150° C. (Torr) |
|---|---|---|---|
| Compound No. 1 | LogP(Torr) = 12.97-5302/T(K) | 0.301 | 2.73 |
| Compound No. 2 | LogP(Torr) = 18.65-7562/T(K) | 0.256 | 5.93 |
| Comparative Compound 3 | LogP(Torr) = 13.93-5842/T(K) | 0.116 | 1.32 |

The results in Table 3 prove that the alkoxide compounds of general formula (I) according to the present invention in which M is silicon have a higher vapor pressure than comparative compound 3 and are superior in vaporization characteristics.

Evaluation Example 4

Evaluation of Vaporization Characteristics of Hafnium Compounds

Vaporization characteristics of compound No. 13 and comparative compound 4 shown below were evaluated by carrying out vapor pressure measurement and calculating the vapor pressures at 150° C. and 200° C. in the same manner as in Evaluation Example 3.

The vapor pressure of comparative compound 4 was unmeasurable because of a failure to obtain a vapor phase even at 210° C. Instead, comparative compound 4 was analyzed by differential thermal analysis (TG-DTA) in a dry argon stream and confirmed to decompose gradually only by heat.

The results obtained of compound No. 13 are shown in Table 4.

TABLE 4

Comparative Compound 4
$$Hf \text{---}(O\text{---}CH_2\text{---}CH_2\text{---}N\diagdown)_4$$

| Compound | Vapor Pressure Equation | Vapor Pressure at 150° C. (Torr) | Vapor Pressure at 200° C. (Torr) |
|---|---|---|---|
| Compound No. 13 | LogP(Torr) = 13.46-5963/T(K) | 0.231 | 7.13 |

The results in Table 4 prove that the alkoxide compound of general formula (I) according to the invention in which M is hafnium has a sufficiently high vapor pressure as a CVD material. In contrast, comparative compound 4 failed to turn to vapor and was found unsuitable as a CVD material.

Example 1

Ethylcyclohexane was dried over metallic sodium wire and purified by distillation in an argon stream. The initial 10 mass % fraction and the final 10 mass % fraction were discarded to obtain a solvent with a water content less than 1 ppm. To 500 ml of the thus prepared solvent were added 0.02 mol of compound No. 2 and 0.1 mol of compound No. 13 in an argon stream to prepare a silicon-hafnium single source for CVD. A hafnium-silicon double oxide film was formed on a silicon wafer using the resulting single source and the CVD system shown in FIG. 1 under the following conditions. The resulting thin film was analyzed for thickness and composition by X-ray fluorescence analysis. The results are shown below.

Film Formation Conditions
  Vaporizer temperature: 170° C.
  CVD material flow rate: 20 mg/min
  Reaction pressure: 667 Pa
  Reaction time: 20 mins
  Substrate temperature: 450° C.
  Carrier Ar gas: 200 sccm
  Annealing conditions after deposition: 600° C.×10 min in 100 sccm oxygen Results of Measurement
  Film thickness: 63 nm
  Composition (by mole): Hf/Si=1.00:0.17

Example 2

Ethylcyclohexane was dried over metallic sodium wire and purified by distillation in an argon stream. The initial 10 mass % fraction and the final 10 mass % fraction were discarded to obtain a solvent with a water content less than 1 ppm. To 500 ml of the thus prepared solvent were added 0.02 mol of compound No. 1 and 0.1 mol of tetrakis(1-methoxy-2-methyl-2-propoxy)hafnium in an argon stream to prepare a silicon-hafnium single source for CVD. A hafnium-silicon double oxide film was formed on a silicon wafer using the resulting single source and the CVD system shown in FIG. 1 under the following conditions. The resulting thin film was analyzed for thickness and composition in the same manner as in Example 1. The results are shown below.

Film Formation Conditions
  Vaporizer temperature: 170° C.
  CVD material flow rate: 20 mg/min
  Reaction pressure: 667 Pa
  Reaction time: 30 mins
  Substrate temperature: 450° C.
  Carrier Ar gas: 200 sccm
  Annealing conditions after deposition: 600° C.×10 min in 100 sccm oxygen Results of Measurement
  Film thickness: 98 nm
  Composition (by mole): Hf/Si=1.00:0.22

Comparative Example 1

Ethylcyclohexane was dried over metallic sodium wire and purified by distillation in an argon stream. The initial 10 mass % fraction and the final 10 mass % fraction were discarded to obtain a solvent with a water content less than 1 ppm. To 500 ml of the thus prepared solvent were added 0.1 mol of tetrakis (1-methoxy-2-methyl-2-propoxy)silicon and 0.1 mol of tetrakis(1-methoxy-2-methyl-2-propoxy)hafnium in an argon stream to prepare a comparative silicon-hafnium single source for CVD. A hafnium-silicon double oxide film was formed on a silicon wafer using the resulting single source and the CVD system shown in FIG. 1 under the following conditions. The resulting thin film was analyzed for thickness and composition in the same manner as in Example 1. The results are shown below.

Film Formation Conditions
  Vaporizer temperature: 170° C.
  CVD material flow rate: 20 mg/min
  Reaction pressure: 667 Pa
  Reaction time: 30 mins
  Substrate temperature: 450° C.
  Carrier Ar gas: 200 sccm
  Annealing conditions after deposition: 600° C.×10 min in 100 sccm oxygen Results of Measurement
  Film thickness: 87 nm
  Composition (by mole): Hf/Si=1.00:0.05

Example 3

Ethylcyclohexane was dried over metallic sodium wire and purified by distillation in an argon stream. The initial 10 mass % fraction and the final 10 mass % fraction were discarded to obtain a solvent with a water content less than 1 ppm. To 500 ml of the thus prepared solvent were added 0.1 mol of compound No. 13 and 0.03 mol of tris(1-dimethylamino-2-methyl-2-propoxy)yttrium in an argon stream to prepare a hafnium-yttrium single source for CVD. A hafnium-yttrium double oxide film was formed on a silicon wafer using the resulting single source and the CVD system shown in FIG. 1 under the following conditions. The resulting thin film was analyzed for thickness and composition by X-ray fluorescence analysis. The results are shown below.

Film Formation Conditions
  Vaporizer temperature: 170° C.
  CVD material flow rate: 20 mg/min
  Reaction pressure: 667 Pa
  Reaction time: 30 mins
  Substrate temperature: 450° C.
  Carrier Ar gas: 200 sccm
  Oxidizing gas: 300 sccm oxygen Results of Measurement
  Film thickness: 100 nm
  Composition (by mole): Hf/Y=1.00:0.25

In Examples 1 to 3, the composition of the resulting thin film is in good agreement with that of the thin film forming material. In contrast, the composition of the thin film obtained in Comparative Example 1 does not agree with that of the thin film forming material. This proves that the alkoxide compounds of the present invention secure satisfactory film composition control.

INDUSTRIAL APPLICABILITY

Use of the material for thin film formation of the present invention containing the alkoxide compound of the present invention realizes formation of a thin film with excellent composition controllability and the like and produces particularly superior effects in the formation of a multi-component thin film by CVD.

The invention claimed is:

1. An alkoxide compound represented by general formula (I)

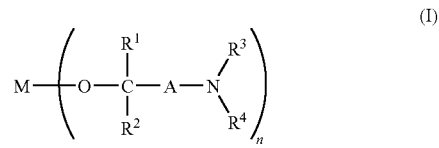

wherein one of $R^1$ and $R^2$ represents an alkyl group having 1 to 4 carbon atoms, and the other represents a hydrogen atom or an alkyl group having 1 to 4 carbon atoms; $R^3$ and $R^4$ each represent an alkyl group having 1 to 4 carbon atoms; A represents an alkanediyl group having 1 to 8 carbon atoms; M represents a hafnium atom; and n represents 4.

2. The alkoxide compound according to claim 1, wherein A in general formula (I) is a methylene group.

3. A material for thin film formation comprising the alkoxide compound according to claim 1.

4. A material for thin film formation comprising the alkoxide compound according to claim 2.

* * * * *